US 9,089,359 B2

(12) United States Patent
Toomey et al.

(10) Patent No.: US 9,089,359 B2
(45) Date of Patent: Jul. 28, 2015

(54) ENDOSCOPIC SYSTEMS AND METHODS FOR RESECTION OF TISSUE

(71) Applicant: COOK MEDICAL TECHNOLOGIES LLC, Bloomington, IN (US)

(72) Inventors: Ciaran Toomey, Rathcormac (IE); Kieran Costello, Ballina-Killaloe (IE)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 167 days.

(21) Appl. No.: 13/716,663

(22) Filed: Dec. 17, 2012

(65) Prior Publication Data
US 2013/0158546 A1    Jun. 20, 2013

Related U.S. Application Data

(60) Provisional application No. 61/577,790, filed on Dec. 20, 2011.

(51) Int. Cl.
*A61B 18/12* (2006.01)
*A61B 17/32* (2006.01)
(Continued)

(52) U.S. Cl.
CPC ... *A61B 17/32002* (2013.01); *A61B 17/320016* (2013.01); *A61B 17/32056* (2013.01); *A61B 18/14* (2013.01); *A61B 18/1492* (2013.01); *A61B 18/1477* (2013.01); *A61B 2017/00269* (2013.01); *A61B 2017/00296* (2013.01); *A61B 2017/32004* (2013.01); *A61B 2018/00202* (2013.01);
(Continued)

(58) Field of Classification Search
CPC .................. A61B 17/320016; A61B 17/32002; A61B 17/32056; A61B 18/14; A61B 18/1477; A61B 18/1492; A61B 2017/00269; A61B 2017/00296; A61B 2017/32004; A61B 2018/00202; A61B 2018/00291; A61B 2018/00601; A61B 2018/144
See application file for complete search history.

(56) References Cited

U.S. PATENT DOCUMENTS 5,375,608 A    12/1994 Tiefenbrun et al.
5,601,572 A *  2/1997 Middleman et al. .......... 606/139
(Continued)

FOREIGN PATENT DOCUMENTS

DE    3313325 A1    10/1984
JP    2000-254146    9/2000
(Continued)

OTHER PUBLICATIONS

International Preliminary Report on Patentability for PCT/US2012-070110 dated Jul. 3, 2014, 9 pgs.
(Continued)

*Primary Examiner* — Michael Peffley
*Assistant Examiner* — Daniel Fowler
(74) *Attorney, Agent, or Firm* — Brinks Gilson & Lione

(57) ABSTRACT

The present embodiments provide apparatus and methods for facilitating endoscopic resection of tissue. In one embodiment, the apparatus comprises a first tube having proximal and distal regions, and a working lumen disposed within at least a portion of the distal region. A second tube is disposed circumferentially around at least a portion of the distal region of the first tube. A wire has a distal end that is securely attached to a distal region of the second tube. In use, rotation of the second tube relative to the first tube causes the wire to pass circumferentially over a distal face of the first tube to incise tissue disposed within the working lumen of the first tube.

17 Claims, 5 Drawing Sheets

(51) Int. Cl.
*A61B 17/3205* (2006.01)
*A61B 18/14* (2006.01)
*A61B 17/00* (2006.01)
*A61B 19/00* (2006.01)
*A61B 18/00* (2006.01)

(52) U.S. Cl.
CPC ............... *A61B2018/00291* (2013.01); *A61B 2018/00601* (2013.01); *A61B 2018/00982* (2013.01); *A61B 2018/144* (2013.01); *A61B 2019/305* (2013.01)

(56) References Cited

U.S. PATENT DOCUMENTS

| 6,086,583 | A  | * | 7/2000 | Ouchi ............... 606/41 |
| 6,238,355 | B1 |   | 5/2001 | Daum |
| 6,394,949 | B1 | * | 5/2002 | Crowley et al. ............... 600/127 |
| 7,303,561 | B2 | * | 12/2007 | Ouchi ............... 606/45 |
| 2004/0210111 | A1 | * | 10/2004 | Okada ............... 600/127 |
| 2008/0125782 | A1 | * | 5/2008 | Rydell et al. ............... 606/79 |
| 2010/0191052 | A1 | * | 7/2010 | Surti et al. ............... 600/106 |

FOREIGN PATENT DOCUMENTS

| WO | WO 2008-067214 A1 | 6/2008 |
| WO | WO 2010-039642 A1 | 4/2010 |

OTHER PUBLICATIONS

PCT International Search Report and Written Opinion for International No. PCT/US2012/070110, date of mailing Apr. 2, 2013, 15 pgs.

\* cited by examiner

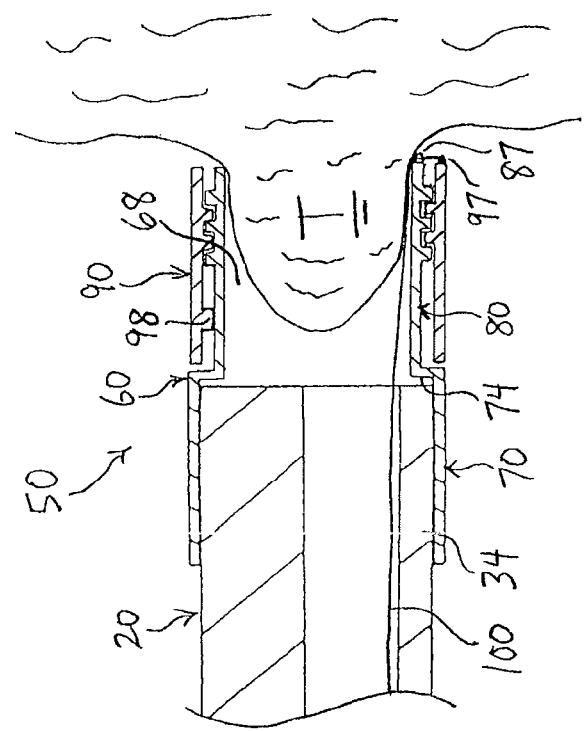
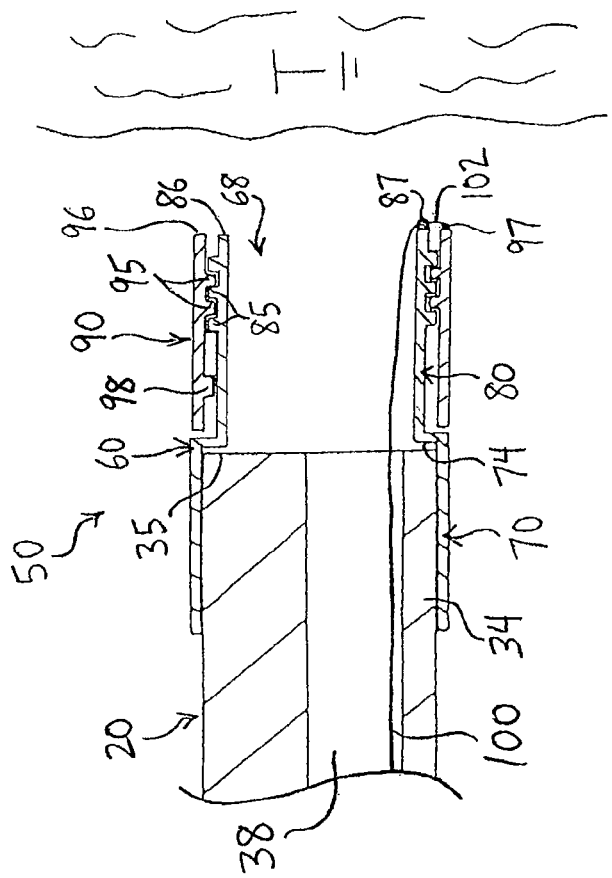

ENDOSCOPIC SYSTEMS AND METHODS FOR RESECTION OF TISSUE

PRIORITY CLAIM

This invention claims the benefit of priority of U.S. Provisional Application Ser. No. 61/577,790, entitled "Endoscopic Systems and Methods for Resection of Tissue," filed Dec. 20, 2011, the disclosure of which is hereby incorporated by reference in its entirety.

BACKGROUND INFORMATION

The present embodiments relate generally to the field of medical devices, and more particularly, to an endoscopic system for resection of tissue.

There are various instances in which it may become necessary or desirable to resect a segment of a patient's tissue, for example, to obtain tissue samples for biopsies, to remove potentially harmful or cancerous localized tissue segments, and the like. In certain procedures, endoscopic mucosal resection of tissue involves using an injection needle or multi-band ligator to create a pseudo-polyp, and then subsequently resecting that tissue using an electrified snare, which is a two-part procedure.

There are various other endoscopic techniques for collecting tissue. For example, one or more cutting instruments, such as a needle knife, may be advanced through a working lumen of an endoscope. The cutting instrument then may be advanced beyond the distal end of the endoscope and actuated by supplying an electrical current to the tip of the instrument. Once heated, the cutting instrument may be positioned to engage and cut the target tissue. The tissue then may be captured and removed, for example, by using a forceps advanced through the working lumen of the endoscope. However, when cutting instruments, such as needle knives, are used in the above-described manner, the result may yield an imprecise cutting of tissue. In particular, a risk exists of improperly maneuvering the cutting instrument and therefore inadvertently cauterizing or searing healthy or non-target tissue. Further, in these procedures, the extended cutting instrument is generally moved in a circular motion, which may increase the risk of incision to the unrelated tissue.

Other instruments, such as needles, may be advanced through a lumen of an endoscope and may engage tissue. For example, a biopsy needle may be used to obtain a sample of tissue. However, such biopsy needles occasionally result in "dry taps," in which a column of tissue is pressed into the needle but not detached from surrounding tissue mass, thereby failing to collect the desired sample tissue.

There is a need for a safe and effective system for the resection of a wide range of tissue segments during endoscopic procedures.

SUMMARY

The present embodiments provide apparatus and methods for facilitating endoscopic resection of tissue. In one embodiment, the apparatus comprises a first tube having proximal and distal regions, and a working lumen disposed within at least a portion of the distal region. A second tube is disposed circumferentially around at least a portion of the distal region of the first tube. A wire has a distal end that is securely attached to a distal region of the second tube. In use, rotation of the second tube relative to the first tube causes the wire to pass circumferentially over a distal face of the first tube to incise tissue disposed within the working lumen of the first tube.

In one embodiment, the wire extends from the distal region of the second tube in a proximal direction through the working lumen of the first tube. An eyelet may be disposed at a distal region of the first tube, such that the wire extends from the distal region of the second tube in a proximal direction through the eyelet and further through the working lumen of the first tube.

The second tube may comprises internal threading and the first tube may comprise external threading, where the internal and external threading enable selective rotation of the second tube relative to the first tube. In alternative embodiments, at least one of the first and second tubes comprises a sharpened distal end configured to puncture tissue and cause the tissue to be subsequently disposed within the working lumen of the first tube. Optionally, the wire may comprise an electrocautery member configured to cauterize a segment of tissue.

In one embodiment, at least a portion of the proximal region of the first tube is adapted to be disposed over an exterior surface of an endoscope. The portion of the proximal region of the first tube that is adapted to be disposed about the exterior surface of the endoscope may comprise an elastic member having a larger diameter state adapted to be placed over the endoscope and a smaller diameter state that permits the first tube to be elastically secured about the exterior surface of the endoscope. The first tube may comprise a stepped portion disposed between the proximal and distal regions, wherein the stepped portion reduces a diameter of the distal region of the first tube, thereby allowing the second tube to be substantially flush with an exterior surface of the proximal region of the first tube.

Advantageously, the tissue resection system of the present embodiments severs only the desired mucosal tissue that is pulled within the working lumen of the first tube. Surrounding mucosal tissue, as well as submucosal tissue, will not be inadvertently incised by the wire. Additionally, the tissue resection system may be faster to use and employ fewer steps than techniques that use a multi-band ligator or injection needle to create a pseudo-polyp and then subsequently resect that tissue using an electrified snare. Still further, in one exemplary method, the tissue resection system allows an enhanced tissue biopsy to be performed, particularly since the number of "dry taps," in which a column of tissue is pressed into the needle but not detached from surrounding tissue mass, may be significantly reduced due to the action of the cutting wire.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 3-4 are side-sectional views of the endoscopic tissue resection system of FIG. 2 with and without tissue drawn into a working lumen of a first tube, respectively.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 1B:
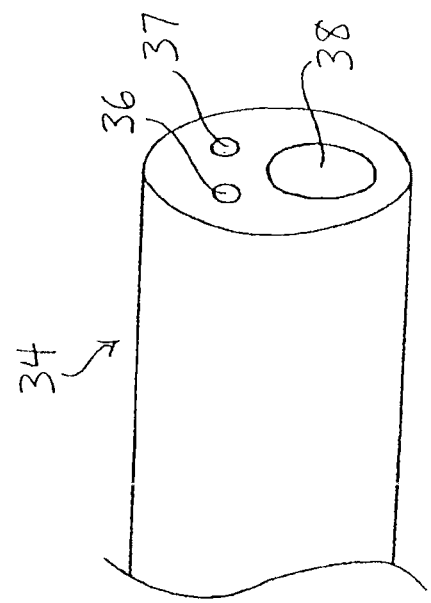
FIGS. 1A-1B are, respectively, a perspective view of an exemplary end-viewing endoscope and a close-up view of the distal region of the endoscope.
Figure 1A:
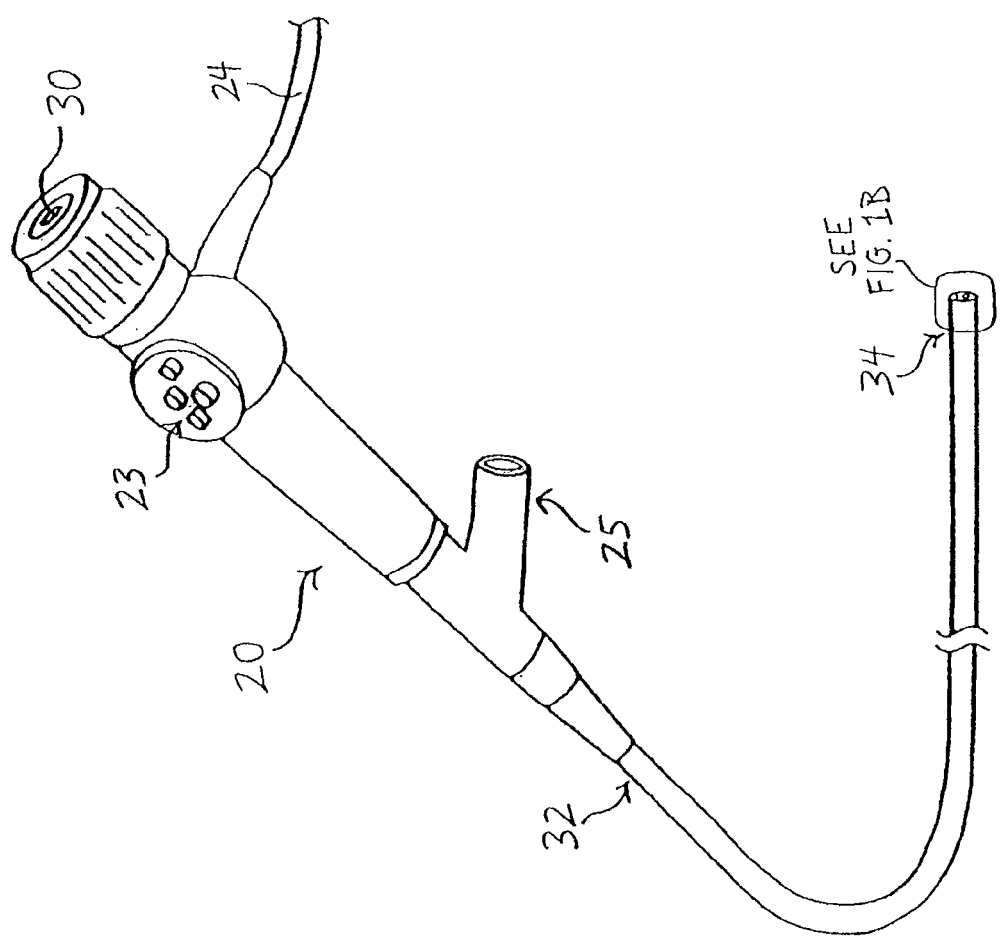

Referring now to FIGS. 1A-1B, an exemplary endoscope 20 is described, which may be used in conjunction with the tissue resection systems described below. In FIG. 1A, the exemplary endoscope 20 comprises an end-viewing endoscope of known construction and having proximal and distal regions 32 and 34, respectively. The endoscope 20 may comprise fiber optic components 36 and 37 for illuminating and capturing an image distal to the endoscope 20, as depicted in FIG. 1B. A physician may view the images distal to the endoscope 20 using an eyepiece 30. A fiber optic cable 24 may be coupled between the endoscope 20 and a suitable light source. A control section 23 may be provided to maneuver the distal region 34 of the endoscope 20, and facilitate actuation of various components associated with the endoscope 20.

The endoscope 20 also may comprise an auxiliary lumen 38, as shown in FIG. 1B. An auxiliary port 25 may be placed in fluid communication with the auxiliary lumen 38, such that components advanced through the auxiliary port 25 are directed into the auxiliary lumen 38. The auxiliary lumen 38 may be sized to accommodate an array of medical components, such as a catheter, forceps, snare and the like. While one auxiliary lumen 38 is shown, additional lumens may be employed. Other features and components of the endoscope 20, and variations thereof, are generally known to those skilled in the art and are not critical to the present invention.

In a conventional procedure, the endoscope 20 may be advanced through a natural bodily lumen, such as the alimentary canal, to a position proximate a target location. A catheter or other medical devices then may be advanced through the auxiliary lumen 38 of the endoscope 20 to the target location. Optionally, a needle or other suitable device may be used to puncture through an organ or a gastrointestinal wall to provide translumenal endoscopic access to various additional bodily regions.

Referring now to FIGS. 2-5, a first embodiment of a tissue resection system 50 is described. In this embodiment, the tissue resection system 50 generally comprises a first tube 60 and a second tube 90. As explained in further detail below, at least one of the first tube 60 and the second tube 90 is coupled to the distal region 34 of the endoscope 20, and the first and second tubes 60 and 90 may be selectively circumferentially rotated with respect to one another.

In one embodiment, the first tube 60 comprises proximal and distal regions 70 and 80. The proximal region 70 of the first tube 60 may be coupled to the distal region 34 of the endoscope 20. In the embodiment of FIGS. 2-5, at least a portion of the proximal region 70 of the first tube 60 is disposed about an exterior surface of the endoscope 20.

Figure 2:
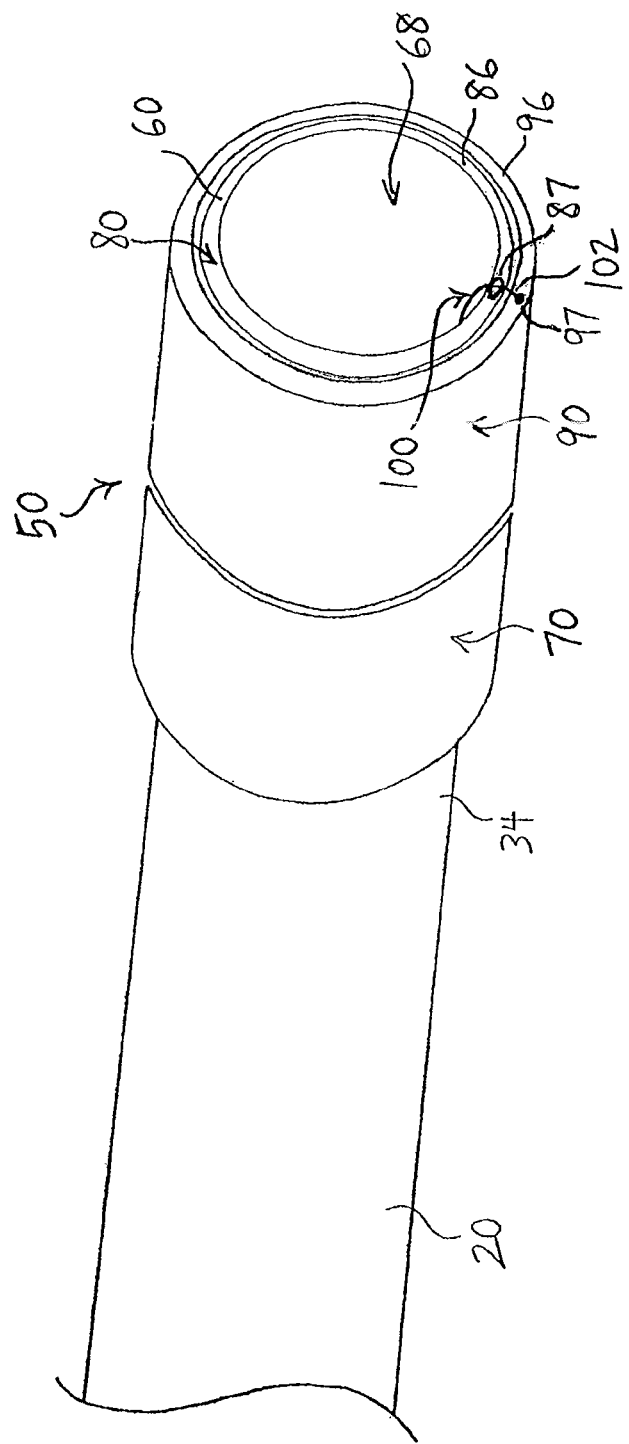
FIG. 2 is an elevated front perspective view of an endoscopic tissue resection system according to a first embodiment.

In one embodiment, at least a portion of the proximal region 70 of the first tube 60 comprises an elastic member having a first inner diameter in a relaxed state, and a second, slightly larger inner diameter when in an expanded state. If the proximal region 70 of the first tube 60 is elastic, it may be sized such that its inner diameter in the relaxed state is slightly smaller than an exterior diameter of the endoscope 20, but its inner diameter in the expanded state is slightly larger than the exterior diameter of the endoscope 20. This configuration allows the proximal region 70 of the first tube 60 to elastically expand to be disposed over the distal region 34 of the endoscope 20. Once in place, the proximal region 70 of the first tube 60 will be allowed to return to its relaxed state, thereby securely engaging the proximal region 70 of the first tube 60 around the exterior surface of the endoscope 20 using a frictional fit, as shown in FIGS. 2-4. An interior surface of the proximal region 70 of the first tube 60 may comprise a texture or material, such as rubber, configured to increase the frictional fit with the exterior surface of the endoscope 20.

If desired, a securing means may be applied to secure a portion of the first tube 60 directly to an exterior surface of the endoscope 20 to prohibit movement of the first tube 60 with respect to the endoscope 20. For example, the securing means may comprise an adhesive tape, heat-shrink tubing, one or more tie-down bands, cable-ties, and the like. The securing means may be configured and disposed so as to not interfere with movement of the endoscope 20 through the patient. Further details of an exemplary securing means and techniques for securing a component, such as the first tube 60, to an exterior surface of an endoscope are explained in U.S. Patent Application Publication Number 2007/0270897, the disclosure of which is hereby incorporated by reference in its entirety.

The distal region 80 of the first tube 60 may comprise a generally tubular shape having a working lumen 68, as shown in FIGS. 2-5. An outer diameter of at least a segment of the distal region 80 of the first tube 60 is less than an inner diameter of at least a segment of the second tube 90, thereby allowing the distal region 80 of the first tube 60 to be generally disposed within the second tube 90, as shown in FIGS. 2-5.

In the embodiment of FIGS. 2-5, the first tube 60 comprises a stepped portion 74, which reduces a diameter of the first tube. The stepped portion 74 may be disposed between the proximal and distal regions 70 and 80 of the first tube 60. In use, the stepped portion 74 is positioned at a location just distal to a distal tip 35 of the endoscope 20, as shown in FIGS. 3-4. The stepped portion 74 portion allows the second tube 90 to be disposed externally about the distal region 80 of the first tube 60 such that the second tube 90 is substantially flush with an exterior surface of the proximal region 70 of the first tube 60, as depicted in FIGS. 2-4. In this manner, the second tube 90 does not substantially increase the radial profile of the endoscope 20 beyond the proximal region 70 of the first tube 60 that is attached to the endoscope 20.

The proximal and distal regions 70 and 80 of the first tube 60 may be integrally formed, or alternatively may comprise two separate generally tubular members that are affixed or coupled together. Accordingly, the first tube 60 may comprise one or more tubular members that are used in conjunction with the second tube 90 to achieve the objectives described in the present application and as explained in further detail below. The stepped portion 74 may afford a transition between materials of the first tube 60, e.g., between a relatively elastic proximal region 70 that may be coupled to the endoscope 20, and a relatively rigid distal region 80 that may support the second tube 90 without bending radially inward.

Alternatively, the stepped portion 74 may be omitted such that the first tube 60 comprises a substantially uniform diameter along its length. In this embodiment, the second tube 90 may increase the outer profile of the overall device beyond the outer diameter of the proximal region 70 of the first tube 60 due to the omission of the stepped portion 74. While the dimensions may be varied, the distal region 80 of the first tube 60 preferably does not interfere with the advancement of components through the auxiliary lumen 38 or the function of fiber optic components 36 and 37 of the endoscope 20, as depicted in FIGS. 3-4.

In an alternative embodiment, the second tube 90 may be secured directly to an outer surface of the endoscope 20. In this alternative, a securing means, as generally described above relative to the first tube 60, may instead be applied to secure a portion of the second tube 90 directly to an exterior surface of the endoscope 20 to prohibit movement of a portion of the second tube 90 with respect to the endoscope 20. In this alternative, the first tube 60 may not have a portion that is secured to the endoscope 20 directly, but rather may be entirely disposed within the second tube 90 at a location that is distal to where the second tube 90 is secured about the endoscope 20.

In one embodiment, the distal region 80 of the first tube 60 and the entirety of the second tube 90 may comprise a relatively rigid material, such as a stainless steel cannula. Alternatively, the distal region 80 of the first tube 60 and the entirety of the second tube 90 may comprise a nickel titanium alloy or other suitable metal or alloy adapted to perform the resection procedure described herein.

In the example of FIGS. 2-5, the distal region 80 of the first tube 60 comprises external threading 85 along at least a portion of its length, and the second tube 90 comprises internal threading 95 along at least a portion of its length. The external and internal threading 85 and 95 permit selective rotation of the first and second tubes 60 and 90 relative to one another, as explained further in FIGS. 5A-5C below.

In one embodiment, at least one of the first tube 60 and the second tube 90 comprises a stop member to limit distal advancement of the first and second tubes 60 and 90 relative to each other. For example, the second tube 90 may comprise a stop member 98, as depicted in FIGS. 3-4, that is disposed proximal to the external and internal threading 85 and 95, such that distal advancement of the second tube 90 is halted when the stop member 98 presses against the external threading 85 of the first tube 60. This safety feature prevents detachment of the second tube 90 distally over the first tube 60, and consequently from the endoscope 20. Additionally, or alternatively, one or more stop members may be disposed on the first tube 60 to prevent detachment of the second tube 90 distally over the first tube 60. Notably, in the embodiment where a stepped portion 74 is provided, proximal detachment of the second tube 90 is inhibited since the second tube 90 will abut the stepped portion 74, thereby providing a proximal movement barrier for movement of the second tube 90.

Referring still to FIGS. 2-5, the tissue resection system 50 further comprises a wire 100 having proximal and distal ends. A distal end 102 of the wire 100 may be secured to an affixation member 97 disposed on a distal face 96 of the second tube 90, as shown in FIGS. 2-5. The affixation member 97 may comprise any suitable mechanism, e.g., a mechanical engagement device, adhesive, solder, or other mechanism, for holding the distal end 102 of the wire 100 in a steady position at the distal face 96 of the second tube 90.

From the affixation member 97, the wire 100 extends proximally through an eyelet 87 disposed on a distal face 86 of the first tube 60, through the working lumen 68 of the first tube 60, and then extends proximally through the auxiliary lumen 38 of the endoscope 20. The proximal end of the wire 100 may be coupled to an actuation mechanism, an electrosurgical unit, or otherwise may be manipulated by a physician.

In one embodiment, the wire 100 may comprise a cauterization wire configured to provide heat, in addition to a mechanical force, to resect tissue. In this example, the wire 100 may comprise one or more wires that may be heated using an electric current, and may be fabricated from any electrically conductive material, including stainless steel. Alternatively, the wire 100 may be fabricated from a shape memory alloy such as nitinol. An electrosurgical generator may be coupled to a proximal region of the wire 100 to provide an electrical energy sufficient to cauterize the tissue. In this embodiment, the wire 100 may be insulated along a portion of its length using an inner sheath.

Rotational movement of the first and second tubes 60 and 90 with respect to one another may be achieved in various ways. In the embodiment of FIGS. 2-5, proximal retraction of the wire 100 relative to the endoscope 20 will impose a force upon the second tube 90 via the affixation member 97. The force imposed upon the second tube 90 by the wire 100, coupled with the threaded engagement between the first and second tubes 60 and 90, will cause the second tube 90 to rotate relative to the first tube 60. The pitch of the external and internal threading 85 and 95 may be varied to facilitate rotation of the second tube 90 relative to the first tube 60 when the wire 100 is proximally retracted. In particular, a pitch of the threading that is more parallel to a longitudinal axis of the device may allow easier rotation of the second tube 90 relative to the first tube 60.

In alternative embodiments, mechanical arrangements may be used to effect rotational movement of the first and second tubes 60 and 90 with respect to one another. Moreover, such mechanisms may be coupled to the first tube 60, the second tube 90, or portions of both tubes, and may be disposed at least partially outside of the body for actuation by the user. In one embodiment, a rigid elongate member may be disposed longitudinally along a length of the endoscope 20, either internal or external to the endoscope 20, and may have a proximal end positioned at least partially outside of the body and a distal end coupled to at least one of the first and second tubes 60 and 90, whereby rotational movement of the proximal end of the elongate member effects rotational movement of the coupled portion of the first and/or second tubes 60 and 90. As a further alternative, such an elongate member may be coupled to a gear or pinion mechanism that is coupled to at least one of the first and second tubes 60 and 90, whereby longitudinally movement of the elongate member effects rotational movement of the gear or pinion coupled to one of the first and second tubes 60 and 90.

Further, the first tube 60 may be moved while the second tube 90 is held stationary, or the second tube 90 may be moved while the first tube 60 is held stationary, or both the first and second tubes 60 and 90 may move simultaneously. In any of these instances, rotational movement of the first and second tubes 60 and 90 with respect to one another can be achieved.

An exemplary method of using the tissue resection system 50 will be described to cauterize target tissue T in a safe and effective manner. In a first step, the endoscope 20 may be retrofitted using the tissue resection system 50 by securing at least a portion of the proximal portion 70 of the first tube 60 to the endoscope 20. For example, the proximal portion 70 may be disposed over the distal region 34 of the endoscope 20 and secured using elastic properties of the proximal portion 70 and/or an external securing means, as noted above.

The endoscope 20 may be advanced to a desired target site using suitable imaging techniques, such as the fiber optic components 36 and 37, an ultrasound transducer, fluoroscopic techniques in conjunction with radiopaque bands, and the like. Once the physician has properly positioned the device adjacent to the target tissue T to be cauterized, a forceps or other suitable grasping instrument may be advanced through the auxiliary lumen 38 of the endoscope 20 and positioned distal to the endoscope to grasp the target tissue T. The forceps or other instrument may be actuated to grasp the target tissue T and then retracted to pull at least a selected portion of the target tissue T into the working lumen 68 within the first tube 60, as depicted in FIG. 4. Alternatively, suction may be applied via the auxiliary lumen 38 to draw the target tissue T into the working lumen 68 within the first tube 60. Advantageously, the fiber optic components 36 and 37 may illuminate and capture an image distal to the endoscope 20 during this process.

Figure 6:
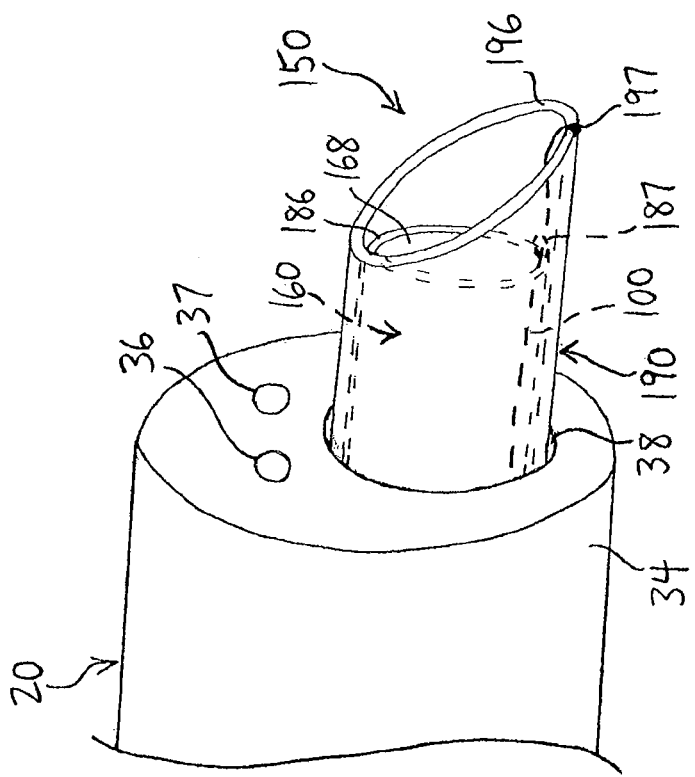
FIG. 6 is a perspective view illustrating a distal region of an alternative tissue resection system.

It should be noted that the target tissue T may be drawn into substantially the entire interior volume of the working lumen 68 within the first tube 60, or alternatively, just a portion of the working lumen 68, as depicted in FIG. 6. If suction is applied via the auxiliary lumen 38, then the target tissue T may be drawn substantially into the entire interior volume of the working lumen 68 within the first tube 60 via the suction. Further, it should be noted that the distal face 86 of the first tubes 60 abuts a segment of the target tissue T just external to the first tube 60, as depicted in FIG. 4.

Figure 5C:
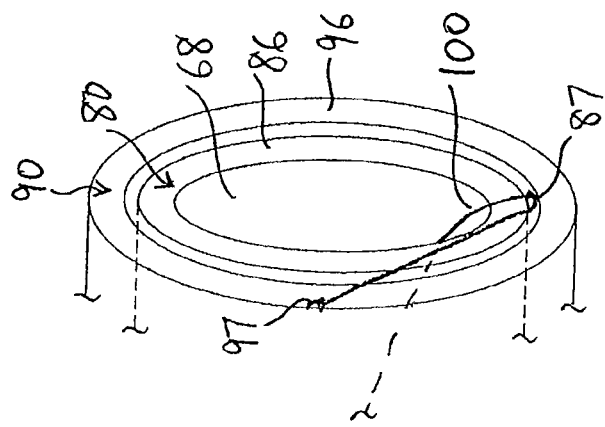
FIGS. 5A-5C are perspective views illustrating a sequential, exemplary use of a distal region of the tissue resection system of FIGS. 2-4.
Figure 5B:
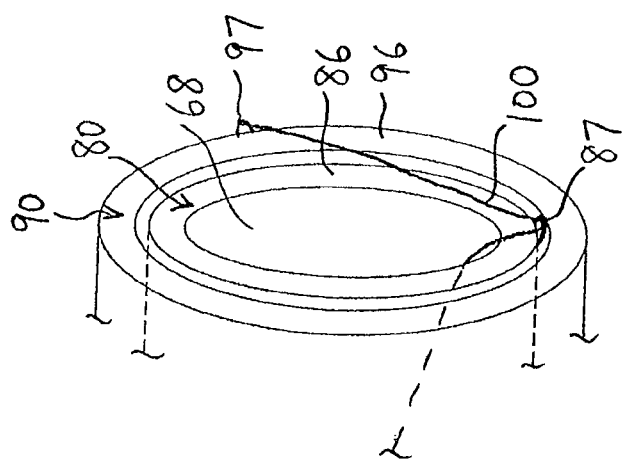
Figure 5A:
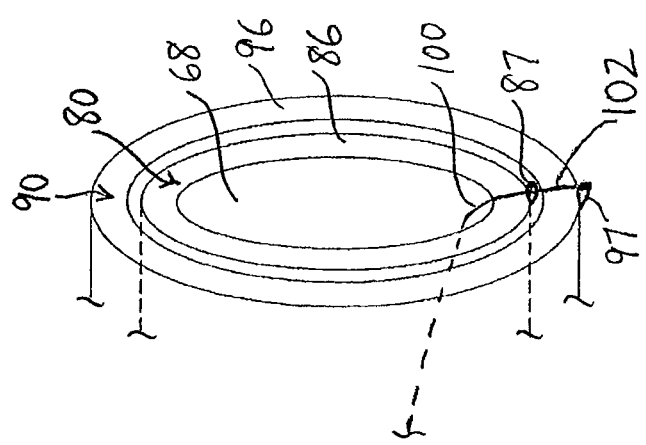

When the desired amount of target tissue T is captured and properly positioned within the first tube 60, the second tube 90 may be rotated relative to the first tube 60, thereby causing the affixation member 97 to move relative to the eyelet 87, and effectively passing the wire 100 circumferentially over the distal face 86 of the first tube 60, as depicted in the sequence shown in FIGS. 5A-5C. In turn, this movement causes the wire 100 to incise the target tissue T disposed within the working lumen 68 of the first tube 60 at a location proximal to the wire 100, thereby separating the target tissue T from the surrounding tissue. Optionally, if the wire 100 is coupled to an electrocautery source, then the heat from the cauterization, in addition to the mechanical force of the wire, further facilitates cutting of the target tissue T.

Advantageously, using the tissue resection system 50 of the present embodiments, only the desired target tissue T that is pulled within working lumen 68 of the first tube 60 is severed. Surrounding mucosal tissue, as well as submucosal tissue, will not be inadvertently incised by the wire 100. The risk of inadvertently incising unwanted tissue may be substantially reduced or eliminated. Additionally, the tissue resection system 50 may be faster to use and employ fewer steps than techniques that use a multi-band ligator or injection needle to create a pseudo-polyp and subsequently resect that tissue using an electrified snare.

In another exemplary procedure, the tissue resection system 50 may be used to segregate an organ from surrounding tissue. For example, to remove an organ such as the gallbladder, portions of the organ may be pulled into the working lumen 68 of the first tube 60, then safely dissected and separated from the liver. In yet other exemplary procedure, internal hemorrhoids, polyps, or other matters may be removed along the gastrointestinal tract, or other matters in other bodily locations.

Figure 7:
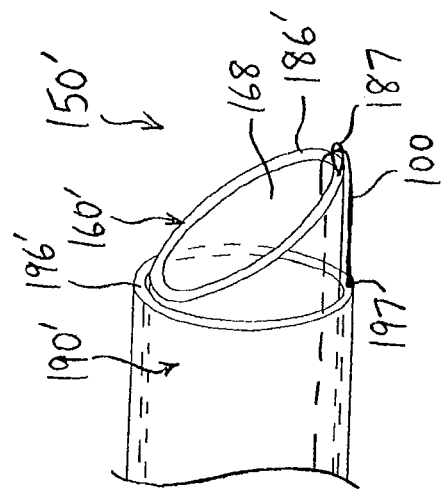
FIG. 7 is a perspective view illustrating a distal region of a further alternative tissue resection system.
Figure 8:
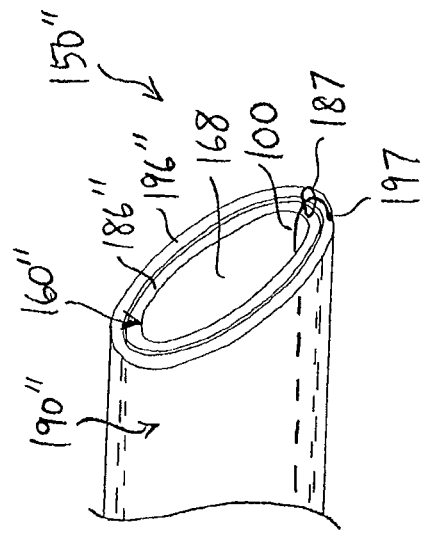
FIG. 8 is a perspective view illustrating a distal region of yet a further alternative tissue resection system.

Referring now to FIGS. 6-8, distal regions of multiple alternative tissue resection systems 150, 150' and 150" are shown and described. The tissue resection systems 150, 150' and 150" of FIGS. 6-8 are particularly well-suited to perform core biopsies, although the systems may be used in other applications.

The tissue resection systems 150, 150' and 150" of FIGS. 6-8 are similar to the tissue resection system of FIGS. 2-5, with a main exception that the systems 150, 150' and 150" are intended to be advanced through the auxiliary lumen 38 of the endoscope 20. Further, one or both of the first and second tubes comprises a sharpened distal face in the embodiments of FIGS. 6-8.

In the embodiment of FIG. 6, the tissue resection systems 150 comprises a first tube 160 having a blunt distal face 186 and a second tube 190 comprising a sharpened distal face 196. Like the embodiment of FIGS. 2-5, a distal end of the wire 100 is secured to an affixation member 197 at a distal region of the second tube 190. The wire 100 then extends proximally through an eyelet 187 coupled to a distal region of the first tube 160, as generally explained above with respect to FIGS. 2-5. The first and second tubes 160 and 190 may comprises a threaded interface, e.g., using internal and external threading 85 and 95 of FIGS. 3-4, to facilitate controlled rotational movement of the first and second tubes 160 and 190 relative to one another.

In an exemplary method of using the tissue resection systems 150 to perform a core biopsy, the endoscope 20 may be advanced to a desired target site using suitable imaging techniques, such as the fiber optic components 36 and 37, an ultrasound transducer, fluoroscopic techniques in conjunction with radiopaque bands, and the like. The tissue resection system 150 is positioned within the confines of the auxiliary lumen 38 during delivery to reduce the risk of damage to bodily passageways. Once the physician has properly positioned the device adjacent to target tissue, the tissue resection system 150 may be advanced distally relative to the endoscope 20 to cause the sharpened distal face 196 of the second tube 190 to pierce through tissue. A segment of tissue then will be disposed within a working lumen 168 of the first tube 160. When the desired amount of tissue is positioned within the first tube 160, the second tube 190 may be rotated relative to the first tube 160, thereby causing the affixation member 197 to move relative to the eyelet 187, and effectively passing the wire 100 circumferentially over the distal face 186 of the first tube 160. In turn, this movement causes the wire 100 to incise the target tissue disposed within the working lumen 168 of the first tube 160 at a location proximal to the wire 100, thereby separating the tissue. Optionally, if the wire 100 is coupled to an electrocautery source, then the heat from the cauterization, in addition to the mechanical force of the wire, further facilitates cutting of the tissue. Notably, in the embodiment of FIGS. 6-8, rotation of the second tube 190 relative to the first tube 160 may be achieved by manually rotating a proximal end of the first tube 160 and/or the second tube 190, which are proximally accessible to a physician as both tubes extend then length of the endoscope 20.

In the embodiment of FIG. 7, the tissue resection system 150' comprises a first tube 160' having a sharpened distal face 186' and a second tube 190' that comprises a blunt distal face 196'. In the embodiment of FIG. 8, the tissue resection system 150" comprises first and second tube 160" and 190" having sharpened distal faces 186" and 196", respectively. Operation of the tissue resection systems of FIGS. 7-8 are otherwise substantially the same as described for FIG. 6 above.

Advantageously, the tissues resection systems of FIGS. 6-8 are well-suited for performing core biopsies as the one or more sharpened distal faces of the first and second tubes can puncture into tissue to surround the target tissue for the biopsy. Moreover, the number of "dry taps," in which a column of tissue is pressed into the needle but not detached from surrounding tissue mass, may be significantly reduced by the action of the cutting wire 100.

As with the system 50 of FIGS. 2-5 above, for the systems 150, 150' and 150" of FIGS. 6-8 it is contemplated that the first tube may be moved while the second tube is held stationary, or the second tube may be moved while the first tube is held stationary, or both the first and second tubes may move simultaneously. Moreover, since proximal ends of the first and second tubes of the systems 150, 150' and 150" of FIGS. 6-8 may extend outside of the body, i.e., the first and second tubes may span a full length within a lumen of the endoscope 20, then a user may directly actuate the proximal ends of the first and second tubes in the embodiments of FIGS. 6-8 to impart the desired rotational motion along the length of the first and/or second tubes.

The above-referenced procedures are only a few examples in which the tissue resection systems 50, 150, 150' and 150" may be used, as it will be apparent that numerous other procedures are possible. Further, the tissue resection systems 50, 150, 150' and 150 provided in accordance with the present embodiments may be used in conjunction with an array of existing commercial endoscopes.

While various embodiments have been described, it will be apparent to those of ordinary skill in the art that many more embodiments and implementations are possible within the scope of the invention. Accordingly, the embodiments are not to be restricted except in light of the attached claims and their equivalents.

We claim:

1. Apparatus for facilitating resection of tissue, the apparatus comprising:
    a first tube having proximal and distal regions, and a working lumen disposed within at least a portion of the distal region;
    a second tube disposed circumferentially around at least a portion of the distal region of the first tube;
    a wire having a distal end securely attached to a distal region of the second tube,
    wherein rotation of the second tube relative to the first tube causes the wire to pass circumferentially over a distal face of the first tube to incise tissue disposed within the working lumen of the first tube,
    wherein the wire extends from the distal region of the second tube in a proximal direction through the working lumen of the first tube; and
    an eyelet disposed at a distal region of the first tube, wherein the wire extends from the distal region of the second tube in a proximal direction through the eyelet and further through the working lumen of the first tube.

2. The apparatus of claim 1 wherein the second tube comprises internal threading and the first tube comprises external threading, where the internal and external threading enable selective rotation of the second tube relative to the first tube.

3. The apparatus of claim 1 wherein the wire comprises an electrocautery member configured to cauterize a segment of tissue.

4. The apparatus of claim 1 wherein at least one of the first and second tubes comprises a sharpened distal face configured to puncture tissue and cause tissue to be disposed within the working lumen of the first tube.

5. The apparatus of claim 1 wherein at least a portion of the proximal region of the first tube is adapted to be disposed over an exterior surface of an endoscope.

6. The apparatus of claim 5 wherein the portion of the proximal region of the first tube that is adapted to be disposed about the exterior surface of the endoscope comprises an elastic member having a larger diameter state adapted to be placed over the endoscope and a smaller diameter state that permits the first tube to be elastically secured about the exterior surface of the endoscope.

7. The apparatus of claim 1 wherein the first tube comprises a stepped portion disposed between the proximal and distal regions of the first tube, wherein the stepped portion reduces a diameter of the distal region of the first tube, thereby allowing the second tube to be substantially flush with an exterior surface of the proximal region of the first tube.

8. The apparatus of claim 1 further comprising an endoscope, wherein the proximal region of the first tube is disposed on a distal end of the endoscope and the distal region of the first tube is disposed distal to the endoscope.

9. The apparatus of claim 1, where at least one of the first and second tubes extend along a full length of an endoscope, where a proximal region of one of the first and second tubes can be directly manipulated by a user.

10. A method for facilitating resection of tissue, the method comprising:
    providing apparatus comprising a first tube having proximal and distal regions, a second tube disposed circumferentially around at least a portion of the distal region of the first tube, and a wire having a distal end securely attached to a distal region of the second tube;
    positioning at least a segment of tissue within a working lumen of the first tube; and
    circumferentially rotating the second tube relative to the distal region of the first tube to pass the wire circumferentially over a distal face of the first tube to incise the segment of tissue disposed within the working lumen of the first tub,
    wherein the wire extends from the distal region of the second tube in a proximal direction through an eyelet disposed at a distal region of the first tube, and then through the working lumen of the first tube.

11. The method of claim 10 wherein the second tube comprises internal threading and the first tube comprises external threading, where the internal and external threading enable selective rotation of the second tube relative to the first tube.

12. The method of claim 10 wherein the wire comprises an electrocautery member, the method further comprising cauterizing the segment of tissue disposed within the working lumen of the first tube.

13. The method of claim 10 wherein at least one of the first and second tubes comprises a sharpened distal end, the method further comprising puncturing tissue using the sharpened distal face to position the tissue within the working lumen of the first tube.

14. Apparatus for facilitating resection of tissue, the apparatus comprising:
    a first tube having a working lumen;
    a second tube disposed circumferentially around at least a portion of the first tube;
    a wire having a distal end securely attached to a distal region of the second tube,
    wherein at least one of the first and second tubes comprises a sharpened distal face configured to puncture tissue such that a segment of tissue is subsequently disposed within the working lumen of the first tube, and
    wherein rotation of the second tube relative to the first tube causes the wire to pass circumferentially over a distal face of the first tube to incise the segment of tissue disposed within the working lumen of the first tube; and an eyelet disposed at a distal region of the first tube, wherein the wire extends from the distal region of the second tube in a proximal direction through the eyelet and further through the working lumen of the first tube.

15. The apparatus of claim 14 wherein the second tube comprises internal threading and the first tube comprises external threading, where the internal and external threading enable selective rotation of the second tube relative to the first tube.

16. The apparatus of claim 14 wherein the wire comprises an electrocautery member configured to cauterize a segment of tissue.

17. Apparatus for facilitating resection of tissue, the apparatus comprising:
- a first tube having proximal and distal regions, and a working lumen disposed within at least a portion of the distal region;
- a second tube disposed circumferentially around at least a portion of the distal region of the first tube;
- a wire having a distal end securely attached to a distal region of the second tube,
- wherein rotation of the second tube relative to the first tube causes the wire to pass circumferentially over a distal face of the first tube to incise tissue disposed within the working lumen of the first tube, and
- wherein the first tube comprises a stepped portion disposed between the proximal and distal regions of the first tube, wherein the stepped portion reduces a diameter of the distal region of the first tube, thereby allowing the second tube to be substantially flush with an exterior surface of the proximal region of the first tube.

* * * * *